United States Patent [19]

Ito et al.

[11] Patent Number: 5,722,969
[45] Date of Patent: Mar. 3, 1998

[54] DISPOSABLE DIAPER

[75] Inventors: Taketo Ito, Utsunomiya; Souiti Fujita, Kawachi-gun; Toshiyasu Tanaami, Tochigi; Taiki Uchiyama, Haga-gun, all of Japan

[73] Assignee: Kao Corp., Tokyo, Japan

[21] Appl. No.: 553,409

[22] PCT Filed: Mar. 20, 1995

[86] PCT No.: PCT/JP95/00511

§ 371 Date: Nov. 22, 1995

§ 102(e) Date: Nov. 22, 1995

[87] PCT Pub. No.: WO95/26174

PCT Pub. Date: Oct. 5, 1995

[30] Foreign Application Priority Data

Mar. 25, 1994 [JP] Japan .................. 6-056325
Apr. 28, 1994 [JP] Japan .................. 6-090980

[51] Int. Cl.$^6$ ............................................. A61F 13/15
[52] U.S. Cl. ..................... 604/390; 604/386; 604/389
[58] Field of Search ........................ 604/385.1, 386–390

[56] References Cited

U.S. PATENT DOCUMENTS

| | | |
|---|---|---|
| 4,210,144 | 7/1980 | Sarge, III et al. . |
| 4,296,750 | 10/1981 | Woon et al. . |
| 5,260,360 | 11/1993 | Mrozinski et al. . |
| 5,352,513 | 10/1994 | Mrozinski et al. . |

FOREIGN PATENT DOCUMENTS

| | | |
|---|---|---|
| 0248600 | 12/1987 | European Pat. Off. . |
| 0286030 | 10/1988 | European Pat. Off. . |
| 0287767 | 10/1988 | European Pat. Off. . |
| 0333441 | 9/1989 | European Pat. Off. . |
| 0440163 | 8/1991 | European Pat. Off. . |
| 55-93802 | 7/1980 | Japan . |
| 56-9402 | 1/1981 | Japan . |
| 63-112704 | 5/1988 | Japan . |
| 5287244 | 11/1993 | Japan . |
| 2054350 | 2/1981 | United Kingdom . |

OTHER PUBLICATIONS

"Derwent Publications Ltd." Week 8948, Apr. 19, 1988, Database WPI & JP.A.01 266 150—Oct. 24, 1989.

*Primary Examiner*—John G. Weiss
*Assistant Examiner*—K. M. Reichle
*Attorney, Agent, or Firm*—Birch, Stewart, Kolasch & Birch, LLP

[57] ABSTRACT

A disposable diaper (1) includes a liquid permeable topsheet (2); a liquid impermeable back sheet (3); an absorbent member (4) interposed between the topsheet and bottom sheet; a fastening tape (10) for securing the diaper (1); and a release tape (30) to which an adhesive surface of the fastening tape is to be adhered. A tensile load of the back sheet (3) at 3% elongation in the transverse direction of the diaper falls within the range of 100 to 300 g/cm. A bulk softness of the back sheet (3) is 55 g or less. A peel strength required to peel the fastening tape (10) from the back sheet at 180° is 400 g/cm or less. The time required until the fastening tape (10) and the back sheet (3) are peeled from each other under a load of 500 g is 10 minutes or longer. An outer surface of the back sheet (3) is not provided with a target tape.

11 Claims, 7 Drawing Sheets

Test Pieces

FIG. 8(b)

Size of Each Test Piece

Test Pieces

DISPOSABLE DIAPER

TECHNICAL FIELD

This invention relates to a disposable diaper. More particularly, it relates to a disposable diaper having no target tape on which a fastening tape is to be adhered during the use of the diaper and having a back sheet whose softness is enhanced, and being free from the problems that the fastening tape is detached or the back sheet is broken during the use.

BACKGROUND ART

Disposable diapers, which have heretofore been commercially available, are designed such that when the diaper is used, a fastening tape for securing the diaper to the user's body may directly be adhered to a back sheet. However, such disposable diapers have the problems that i) the back sheet is broken during the use of the diaper, ii) the fastening tape once adhered is often detached during the use of the diaper, and/or iii) the softness of the back sheet is low. Therefore, most of the disposable diapers, which are commercially available at present, are provided with a target tape on which the fastening tape is to be adhered. The primary object of the target tape is to prevent the back sheet from being broken when the fastening tape once adhered is detached from the back sheet.

In the diapers provided with the target tapes, the fastening tape is required to be adhered to the target tape. However, when the mother puts the diaper on the baby, she happens to adhere the fastening tape directly to the back sheet by mistake. This is likely to cause the back sheet to be broken. Further, limitation is imposed on the adjustment in the waist size of the diaper because adhesion of the fastening tape is limited only onto the target tape.

Therefore, recently, several types of disposable diapers having no target tape have been proposed.

In these disposable diapers, prevention of breakage of the back sheet is intended by reducing the peel strength of the fastening tape or increasing the mechanical strength of the back sheet. However, if the peel strength of the fastening tape is reduced, the problems will be raised that the fastening tape once adhered is detached while the wearer moves although the breakage of the back sheet can be prevented. If the mechanical strength of the back sheet is increased, the back sheet provides an unpleasant stiff feeling. Such problems restricts the user of the disposable diapers of this type to those who move rather calmly, such as adults and few-month-old babies.

Further, in order to solve the above problems, some technological thoughts have been proposed as to the disposable diapers having no target tape.

For example, Japanese Patent Application Laid-open 5-287244 discloses a tape system for use as a fastening tape for diapers, wherein the retention time, the shear strength and the peel strength of an adhesive agent layer of the type are specified. Japanese Patent Application Laid-opens 55-93802 and 56-9402 disclose disposable diapers having a reinforced back sheet and no target tape.

However, the above-mentioned Japanese Patent Application Laid-open 5-287244 indicates nothing about a back sheet. The tape system disclosed fails to exhibit its inherent performance sufficiently when used in combination with a conventional back sheet. Further, the diaper disclosed therein fails to enhance the softness and the comfortableness of the back sheet. Disposable diapers disclosed in the above-mentioned Japanese Patent Application Laid-opens 55-93802 and 56-9402 have a reinforced back sheet.

However, the diapers fail to exhibit their inherent performance so far as no limitation is imposed on the strength of the back sheet or the peel strength of the fastening tape because the reinforcement is effected by the adhesive agents such as hot melt.

DISCLOSURE OF THE INVENTION

Therefore, an object of the present invention is to provide a disposable diaper having no target tape, thereby preventing breakage of the back sheet or detachment of the fastening tape even when the diaper is subjected to the vigorous motion of the wearer, and enhancing flexibility of the back sheet and comfortableness during the use of the diaper.

The inventors carried out extensive research about disposable diapers having no target tape and found that the object can be accomplished by specifying the relationship between the physical properties of the back sheet and the physical properties of the fastening tape. The present invention is based on such findings.

Specifically, the present invention provides a disposable diaper comprising:

a liquid permeable topsheet;

a liquid impermeable back sheet;

an absorbent member interposed between said topsheet and said back sheet;

a fastening tape for securing said diaper when said diaper is worn by the wearer, said fastening tape being provided with a folding section at which said fastening tape is to be folded back; and a release tape to which, when said fastening tape is not in service and is folded back, an adhesive surface of said fastening tape is to be adhered, said disposable diaper being characterized in that:

a tensile load of said back sheet at 3% elongation in the transverse direction of said disposable diaper falls within the range of 100 g/cm to 300 g/cm, and a bulk softness of said back sheet is 55 g or less;

a peel strength required to peel said fastening tape from said back sheet at 180° is 400 g/cm or less, said peel strength being measured after said fastening tape adhered to said back sheet has been allowed to stand for 24 hours at 40° C. and 80% RH, and a time required until said fastening tape and said back sheet are peeled from each other under a load of 500 g is 10 minutes or longer; and an outer surface of said back sheet is not provided with a target tape to which, when said fastening tape is in service, the adhesive surface of said fastening tape is to be adhered.

With the disposable diaper in accordance with the present invention, the outer surface of the back sheet is not provided with a target tape. When the disposable diaper in accordance with the present invention is to be used, the fastening tape is directly adhered to the back sheet. The fastening tape and the back sheet have the specific physical properties. Therefore, the back sheet is not broken or the fastening tape once adhered is not detached during the use of the diaper.

Further scope of applicability of the present invention will become apparent from the detailed description given hereinafter.

However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present inveniton will become more fully understood from the detailed description given hereinbelow and the accompanying drawings which are given by way of illustration only, and thus are not limitative of the present invention, and wherein.

DETAILED DESCRIPTION OF THE INVENTION

The present invention will hereinbelow be described in further detail with reference to the accompanying drawings. It should be understood that the present invention is not limited thereto.

Figure 1:
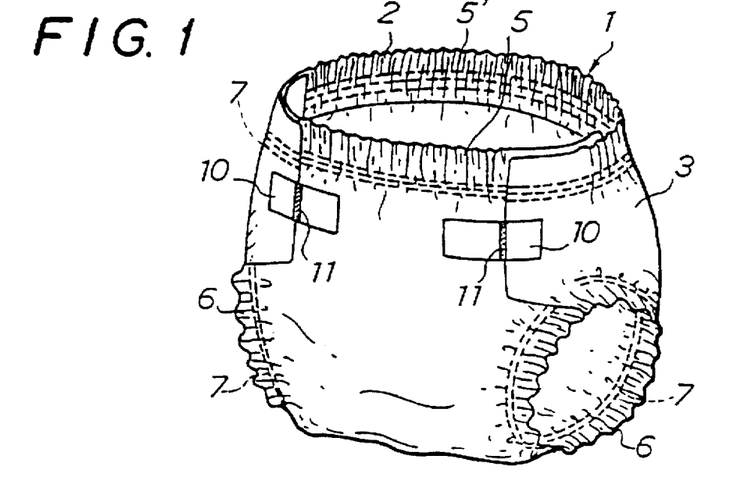
FIG. 1 is a perspective view showing the front side (stomach side) of a disposable diaper in accordance with an embodiment of the present invention.
Figure 2:
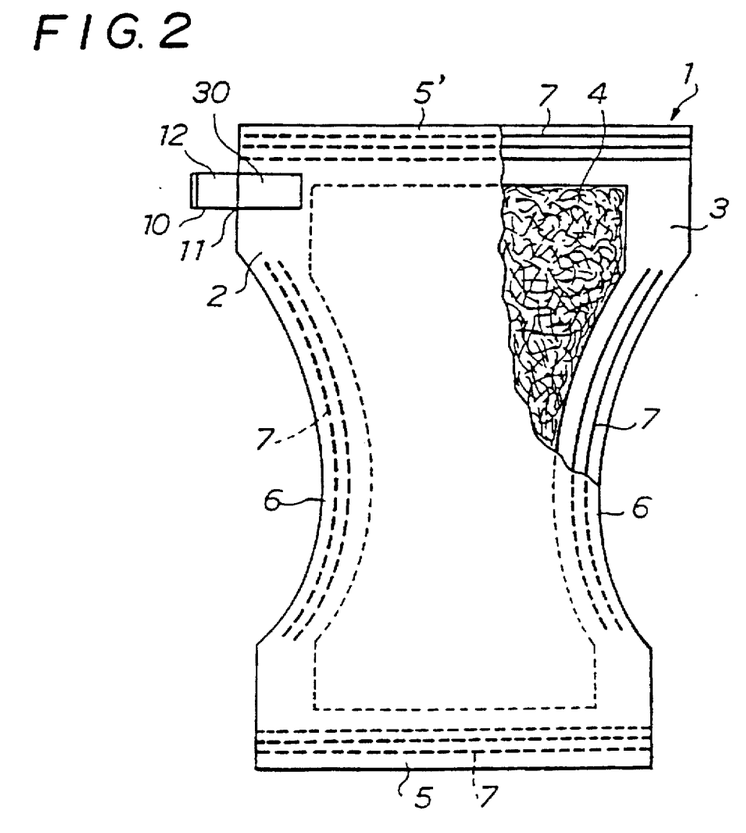
FIG. 2 is a cut away view in which the disposable diaper shown in FIG. 1 is laid flat.

FIG. 1 is a perspective view showing the front side (stomach side) of a disposable diaper in accordance with an embodiment of the present invention. FIG. 2 is a view in which the disposable diaper shown in FIG. 1 is laid flat.

The disposable diaper according to the embodiment illustrated in FIG. 1 comprises a liquid permeable topsheet 2, a liquid impermeable back sheet 3 and an absorbent member 4 interposed between the topsheet 2 and the back sheet 3.

The disposable diaper 1 also comprises a fastening tape 10 for securing the diaper 1 when the diaper 1 is worn by the wearer. The fastening tape 10 is provided with a folding section 11 at which the fastening tape 10 is to be folded back. The disposable diaper 1 further comprises a release tape 30 (shown in FIG. 2) to which, when the fastening tape 10 is not in service and is folded back, an adhesive surface of the fastening tape is to be adhered.

In the disposable diaper of the present invention, a tensile load of the back sheet 3 at 3% elongation in the transverse direction of the disposable diaper 1 falls within the range of 100 g/cm to 300 g/cm;

the bulk softness of the back sheet 3 is 55 g or less;

a peel strength required to peel the fastening tape 10 from the back sheet 3 at 180° is 400 g/cm or less, the peel strength being measured after the fastening tape 10 adhered to the back sheet 3 has been allowed to stand for 24 hours at 40° C. and 80% RH;

a time required until the fastening tape 10 and the back sheet 3 are peeled from each other under a load of 500 g (hereinafter sometimes referred to as "retention time") is 10 minutes or longer; and an outer surface of the back sheet 3 is not provided with a target tape to which, when the fastening tape is in service, the adhesive surface of said fastening tape is to be adhered.

The term "outer surface" as used herein means a surface of the back sheet facing outwardly when the diaper is worn.

More specifically, as illustrated in FIGS. 1 and 2, the region of the absorbent member 4 corresponding to the crotch portion is curved in a constricted hourglass shape. Also, the regions of the topsheet 2 and the back sheet 3 corresponding to the crotch portion are curved in a constricted hourglass shape in accordance with the shape of the absorbent member 4. The absorbent member 4 is interposed and secured by the topsheet 2 and the back sheet 3. Further, elastic expansible members 7 are located at the portions extending beyond the peripheral portions of the absorbent member 4 and corresponding to the front and back waist portions 5, 5' and the leg portions 6. When the diaper is worn by the wearer, the elastic expansible members 7 serve to fit the waist portions 5, 5' and the leg portions 6 to the wearer's body. The elastic expansible members 7 are secured by the topsheet 2 and the back sheet 3.

The materials of the members constituting the disposable diaper 1 are described below.

Specifically, as the topsheet 2, a liquid-permeable sheet, which allows the discharged matter to permeate into the absorbent member 4 and gives a feeling like an underwear, is preferably used. Examples of such liquid-permeable sheets include woven fabrics, nonwoven fabrics, and perforated films. The peripheral regions of the topsheet 2 may be subjected to water-repellent finishing so that the body fluids such as urine may not seep and leak from the peripheral regions of the topsheet 2. For this purpose, a hydrophobic compound such as silicone oil and paraffin wax may be coated on the peripheral regions of the topsheet 2. Alternatively, a hydrophilic compound such as an alkyl phosphate may be coated on the entire area of the topsheet 2, and the peripheral regions of the topsheet 2 may then be washed with hot water.

As the absorbent member 4, a combination of comminuted pulp, which serves as a predominant component, and a superabsorbent polymer is preferably used. The superabsorbent polymer may be located at any of an upper layer, the middle layer, and a lower layer in the absorbent member 4. Also, the superabsorbent polymer may be mixed with the pulp. The superabsorbent polymer is preferably capable of absorbing and retaining an amount of a liquid at least 20 times as large as the weight of the polymer and is preferably in the form of particles having the gelation properties. Preferred examples of such superabsorbent polymers include a starch-acrylic acid (or acrylate) graft copolymer, a saponification product of a starch-acrylonitrile copolymer, a crosslinking product of sodium carboxymethylcellulose, and an acrylic acid (or acrylate) polymer.

The elastic expansible members 7 are preferably made of rubber in the form of string, ribbon or film, or foamed polyurethane in the form of film. The elastic expansible members 7 preferably have a stress at 150% elongation falling within the range of 40 g to 150 g.

The fastening tape 10 has an adhesive surface 12 provided with an adhesive agent such as a rubber adhesive agent, an acrylic adhesive agent and a silicone adhesive agent. No limitation is imposed on the adhesive agent so far as the above-mentioned physical properties are satisfied. The rubber adhesive agent includes, for example, an adhesive agent containing natural rubber or synthetic rubber as a main component. In particular, from the point of view of eliminating pollution by hot-melt coating, an adhesive agent containing an ABA or AB type of block copolymer as a main component is preferred, wherein A represents a thermoplastic segment, and B represents the rubber segment. Examples of such block copolymers include a styrene-isoprene-styrene copolymer, a styrene-butadiene-styrene copolymer, a styrene-ethylene-butadiene-styrene copolymer, styrene-butadiene copolymer, and hydrogenation products of these copolymers.

No limitation is imposed on the acrylic adhesive agent. Examples of the acrylic adhesive agent include a polymer obtained by copolymerization of a major amount of a monomer which forms a soft segment having a low Tg and therefore imparts adhesive properties, a small amount of a monomer which forms a hard segment having a high Tg and therefore imparts adhesive properties and cohesive force, and a minor amount of a monomer which has functional groups and therefore improves crosslinking and adhesive properties.

Examples of the monomers used in the major amount in the copolymerization include ethyl acrylate (EA), butyl acrylate (BA), and 2-ethylhexyl acrylate (2-EHA). Examples of the monomers used in the small amount in the copolymerization include vinyl acetate (VAc), acrylonitrile (AN), acrylamide (AM), styrene (St), methyl methacrylate (MMA), and methyl acrylate (MA). Examples of the monomers used in the minor amount in the copolymerization include methacrylic acid (MAA), acrylic acid (AA), itaconic acid (IA), hydroxyethyl methacrylate (HEMA), hydroxypropyl methacrylate (HPMA), dimethylaminoethyl methacrylate (DM), acrylamide (AM), methylolacrylamide (N-MAN), glycidyl methacrylate (GMA), and maleic anhydride.

The thickness of the adhesive surface is not limited to a specific value. Generally, the thickness of the adhesive surface preferably falls within the range of 10 to 100 μm.

No limitation is imposed on a support of the fastening tape and it includes, for example, films and tapes. Preferred examples of the support include a plastic material containing polypropylene as disclosed in, for example, Japanese Patent Application Laid-open 63-112704, a laminate of polypropylene and a polypropylene-containing plastic material, or a polyester. The surface of the film and the tape may be flat or a mat-like surface. It is also possible to use a foamed support or a support having an uneven surface. Where a film is used as the support and the film contains, as the main component, an olefin elastomer, a styrene elastomer, a urethane elastomer, or a polyester elastomer, good slipping properties can be obtained, and the fastening tape can be rendered soft. The thickness of the support falling within the range of 50 μm to 150 μm is preferred in view of practical use.

The back sheet 3 may be any material so far as the above-described physical properties are satisfied. In particular, the back sheet 3 preferably has a break strength in the transverse direction of the disposable diaper of 250 g/cm or greater. If the break strength is smaller than 250 g/cm, the back sheet is unfavorably caused to be broken when the fastening tape is peeled from the back sheet.

Further, the back sheet 3 preferably comprises a moisture (water vapor) permeable porous sheet because the porous sheet is more advantageous in prevention of stuffiness. A moisture permeability of the porous sheet preferably falls within the range of 0.5 to 4.0 g/100cm$^2$. hr.

The moisture permeability is measured in the manner described below. The moisture permeability is measured in accordance with JIS Z-0208. Specifically, the measurement conducted with the following (1) device and implements, (2) agent and (3) test pieces, and in accordance with the following (4) procedure and (5) calculation formula.

(1) Device and implements
  i) Moisture-permeable cup.
  ii) Thermo-hygrostat: A device, in which the temperature and humidity are kept at prescribed values, and air can circulate through the test piece at a speed of 0.5 to 2.5 m/s.
    Conditions in the thermo-hygrostat: Temperature 30° C., relative humidity 90±2% (dry-bulb temperature 30 ° C., wet-bulb temperature 28.6° C.)
  iii) Balance: Balance having a sensitivity of 0.01 g/div.
  iv) Water bath.
  v) Desiccator.
  vi) Sieve: U.S. Tyler standard sieve (7 mesh, 28 mesh).

(2) Agents
  i) Absorbing agent: Calcium chloride (for U-tube) having a particle size such that the particles can pass through 2.380μ(7 mesh) and cannot pass through 590μ(28 mesh).
  ii) Sealing wax agent: A mixture of 80 wt.% of paraffin wax having a melting point of 50 to 52° C. and 20 wt.% of viscous polyisobutylene (low polymerization degree). When a moisture-permeable cup is used, 160 g of paraffin wax and 40 g of viscous polyisobutylene are measured. They are then heated on the water bath, melt blended together at a temperature of approximately 100° C. The resulting mixture is used as the sealing wax agent. When the sealing wax agent is to be used, it is heated to a temperature of approximately 60° C. to 70° C.
  iii) n-Heptane: Used to remove the sealing wax agent from the moisture-permeable cup.

(3) Test pieces
  i) Test pieces are circular pieces having a diameter (approximately 70 mm) greater than the inner diameter of the moisture-permeable cup used. Four test pieces are cut from a single sample and prepared for the test.
  ii) The thicknesses at five points of each test piece are measured.

(4) Procedure
  i) The absorbing agent is put into the moisture-permeable cup, and the moisture-permeable cup is covered with a ring provided with the test piece. The molten sealing wax agent is poured into the groove at the periphery of the cup, and the moisture-permeable cup and the ring are thereby secured to each other. The resulting combination of the moisture-permeable cup and the ring is used as a specimen.

ii) A number is marked on the side surface of the moisture-permeable cup. The specimen is allowed to stand for 30 minutes in the desiccator, and the weight $W_0$ of the specimen is then measured.

iii) The specimen is put into the thermo-hygrostat kept under the prescribed test conditions. After the specimen has been allowed to stand for one hour in the thermo-hygrostat, the specimen is taken out of the thermo-hygrostat and allowed to stand in the desiccator. After the specimen has been allowed to stand for 5 minutes in the desiccator, the specimen is taken out of the desiccator, and the weight $W_1$ of the specimen is measured.

(5) Calculation

The moisture permeability is calculated by converting the change in weight ($W_1-W_0$) after one hour into the value for a moisture permeation area of 100 cm². The moisture permeation area of the moisture-permeable cup is 28.27 cm².

Moisture permeability=$[(W_1-W_0)/28.27]\times 100$=$(W_1-W_0)\times 3.54$[in units of g/100 cm².1 hr]

As the porous sheet, a porous sheet which is described below and has the foregoing physical properties is preferably used.

The porous sheet is obtainable by preparing, by melt blending, a melt blended solution comprising crystalline polyolefin and a compound with which the crystalline polyolefin is miscible and in which the crystalline polyolefin will dissolve at or above the melting point of the crystalline polyolefin but which will phase separate below the melting point of the crystalline polyolefin, molding the melt blended solution into a sheet, and stretching the sheet at least in one direction to form micropores.

As the crystalline polyolefin used for the formation of the porous sheet, a polypropylene is preferably used which has a ratio of the weight-average molecular weight Mw to the number-average molecular weight Mn of Mw/Mn>5.0. The preferred ratio is Mw/Mn>6.0.

The ratio serves as an index representing the distribution of the molecular weight. If the ratio is Mw/Mn>5.0, for example, when at least 20 wt.% of mineral oil serving as the compound is melt blended with the polypropylene, the mineral oil can be quickly dissolved in the polypropylene and can be stably mixed with the polypropylene. Therefore, the ratio is preferably Mw/Mn>5.0.

Also, the weight-average molecular weight of the polypropylene preferably falls within the range of 300,000 to 600,000. The melting point of the polypropylene preferably falls within the range of 155° to 170° C.

The polypropylene may be of a homogeneous type, a block type, or a random type. These types of polypropylenes may be used alone or as a mixture of two or more of them. These types of polypropylenes may also be used as a mixture with other polymers such as polyethylene.

In addition to satisfying the above ratio Mw/Mn>5.0, the polypropylene still preferably satisfies and the relationship between the isotactic pendant content(P) and the melt index (MI) of 1.00>P>0.015 log MI+0.955 because the polypropylene can exhibit high crystallinity and improved rigidity.

The isotactic pendant content (P) is indicative of crystallinity of the propylene.

The melt index (MI) preferably falls within the range of 0.03 to 2.0 g/10 minutes.

If the MI is lower than 0.03, the flow properties of the melt during the granulation or molding process will be low, and therefore a high mechanical power will be required. Accordingly, the MI of lower than 0.03 is not advantageous in terms of economy and production speed. If the MI is higher than 2.0, the melt tension is reduced. Therefore, for example, when a sheet is formed by an inflation molding, the blown film cannot be lifted easily, and the inflation molding becomes unstable. Therefore, the above range is preferred.

Insofar as the characteristics described above are obtained, the compound is not limited to a specific one. Preferred examples of such compounds include mineral oil, such as liquid paraffin, synthetic lubricating oil, dioctyl phthalate, diethyl phthalate, triethylene glycol, dibutyl phthalate, and esters of phthalic acid, trimellitic acid, pyromellitic acid, and/or an aliphatic polybasic carboxylic acid with an alkyl alcohol.

When forming the porous sheet, the proportions of the crystalline polyolefin and the compound is such that the proportion of the crystalline polyolefin falls within the range of 30 to 90 parts by weight, preferably 60 to 80 parts by weight, and the proportion of the compound falls within the range of 70 to 10 parts by weight, preferably 40 to 20 parts by weight.

If the proportion of the crystalline polyolefin is smaller than 30 parts by weight, the shaping properties of the sheet after the orientation will be poor because the proportion of the matrix polymer is low. Therefore, the problems will be often raised that, when the sheet is wound up into a roll, the micropores are collapsed, or a liquid such as the mineral oil bleeds out. If the proportion of the crystalline polyolefin is greater than 90 parts by weight, the problems will be often raised that, even if the sheet can be oriented, the micropores imparting the moisture permeability cannot be formed. Therefore, the proportion of the crystalline polyolefin preferably falls within the above range.

The temperature suitable for melt blending is at or above the melting point of the crystalline polyolefin, preferably ranging from 180° to 250° C. Melt blending for preparing a melt blended solution can be carried out by a twin-screw extruder. Polypropylene pellets are fed into a hopper in an constant amount, while the compound is fed into the vent of the twin-screw extruder.

In order to form the sheet, the solution may be cooled, and compounded pellets may be formed. Thereafter, a sheet may be formed by the inflation molding from a circular die with a single-screw extruder. Alternatively, a twin-screw extruder may be used, and the inflation molding may be carried out with a circular die connected via a gear pump to the leading end of the twin-screw extruder.

During the formation of the sheet, if desired, for example, various additives described below may be added in amounts falling within the ranges described below.

Specifically, a nucleating agent for controlling the crystal size of the polypropylene, such as p-tert-butylbenzoic acid aluminum salt, 1, 2, 3, 4-dibenzylidenensorbitol, or 1, 2, 3, 4-di-(p-ethylbenzylidene)sorbitol, may be added in a proportion of 0.5 wt.% or less, based on the total amount of the solution. Also, a breakage preventing inorganic filler, such as anhydrous silica or zeolite, may be added in a proportion of 1 wt.% or less, based on the total amount of the solution. Further, an inorganic filler for imparting the hiding properties, such as titanium oxide, barium sulfate, calcium carbonate, or talc, may be added in a proportion of 20 wt.% or less, based on the total amount of the solution. Furthermore, a coloring agent, such as phthalocyanine blue, quinacridone red, dioxazine violet and isoindolenone, may be added in a proportion of 0.05 wt.% or less, based on the total amount of the solution.

In cases where the nucleating agent is added, it is preferably added as a nucleating agent master batch.

During the orientation, the draw ratio preferably falls within the range of between 1.2 and 3, and orientation temperature preferably falls within the range of 10° to 80° C. The orientation may be monoaxial or biaxial.

The pore diameter of the micropores formed by the orientation preferably falls within the range of 0.05 to 1 μm.

The disposable diaper 1 in accordance with the present invention has the features described below. Specifically, a tensile load of the back sheet at 3% elongation in the transverse direction of the disposable diaper 1 falls within the range of 100 g/cm to 300 g/cm, and preferably within the range of 100 g/cm to 200 g/cm. Also, a bulk softness of the back sheet in the transverse direction of the disposable diaper is 55 g or less, and is preferably 45 g or less, and more preferably falls within the range of 30 to 40 g. Further, a break strength of the back sheet 3 in the transverse direction of the disposable diaper is preferably 250 g/cm or more, and more preferably falls within the range of 300 to 1,000 g/cm. A peel strength required to peel the fastening tape 3 from the back sheet at 180° is 400 g/cm or less, the peel strength being measured after the fastening tape adhered to the back sheet 3 has been allowed to stand for 24 hours at 40° C. and 80% RH, and preferably falls within the range of 150 to 300 g/cm. Also, a time required until the fastening tape 10 and the back sheet are peeled from each other under a load of 500 g is 10 minutes or more, and preferably falls within the range of 30 to 600 minutes, and more preferably falls within the range of 60 to 600 minutes. Further, the outer surface of the back sheet 3 is not provided with a target tape to which, when the fastening tape 10 is in service, the adhesive surface of the fastening tape is to be adhered.

Specifically, the disposable diaper in accordance with the present invention is characterized by combining the back sheet having the foregoing physical properties and the fastening tape having the foregoing physical properties. The disposable diaper in accordance with the present invention need not be provided with a target tape. The disposable diaper in accordance with the present invention is has a soft feeling and a good fit.

If the tensile load of the back sheet at 3% elongation in the transverse direction of the disposable diaper 1 is smaller than 100 g/cm, when the fastening tape is subjected to a load during the use of the diaper, the back sheet will readily elongate excessively, and the fastening tape cannot follow up the elongation of the back sheet. Therefore, the fastening tape will be detached, or the elongated portion of the back sheet will be broken. If the tensile load of the back sheet at 3% elongation in the transverse direction of the disposable diaper 1 is greater than 300 g/cm, the back sheet cannot readily elongate and cannot follow up the motion of the wearer. Therefore, a good fit cannot be obtained.

If the bulk softness of the back sheet is more than 55 g, the softness of the back sheet will be bad. Therefore, the entire diaper will give an unpleasant stiff feeling.

If the peel strength required to peel the fastening tape from the back sheet at 180° is greater than 400 g/cm, the back sheet will break when the fastening tape is detached from the back sheet after the diaper has been worn by the wearer.

If the time required until the fastening tape and the back sheet are peeled from each other under a load of 500 g is shorter than 10 minutes, when the wearer moves vigorously or sits down, a stress will be exerted on the fastening tape, and the fastening tape will be detached from the back sheet. As a result, leakage of the discharged matter will occur.

The term "target tape" as used herein refers to any adherent member on which the fastening tape is to be adhered in a conventional disposable diaper and should not be particularly limited in shape or material.

Figure 3:
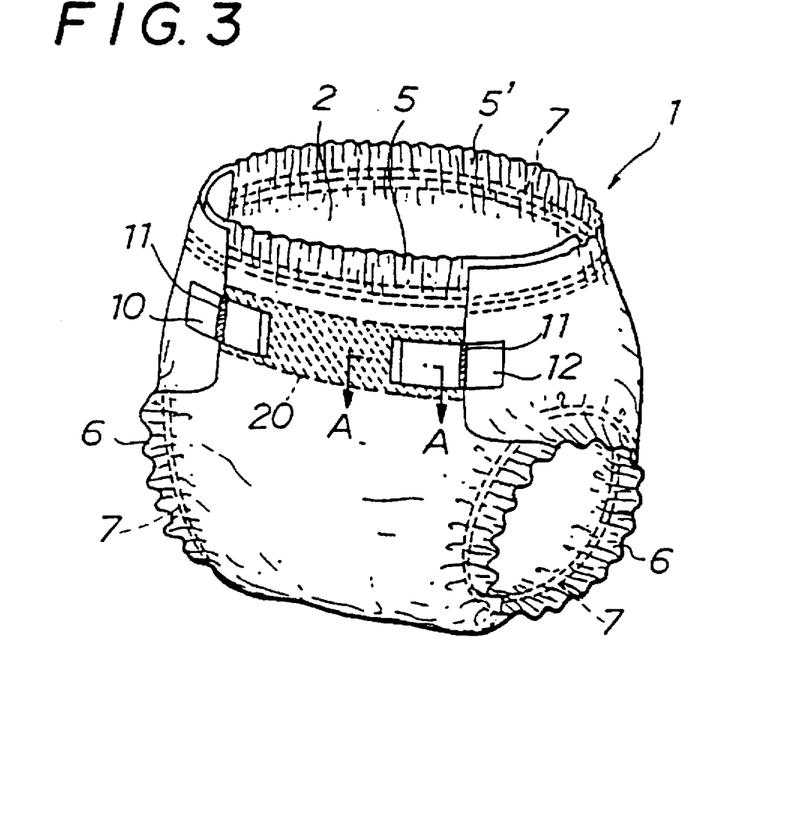
FIG. 3 is a perspective view showing a front side (stomach side) of the disposable diaper according to another embodiment of the present invention.
Figure 4:
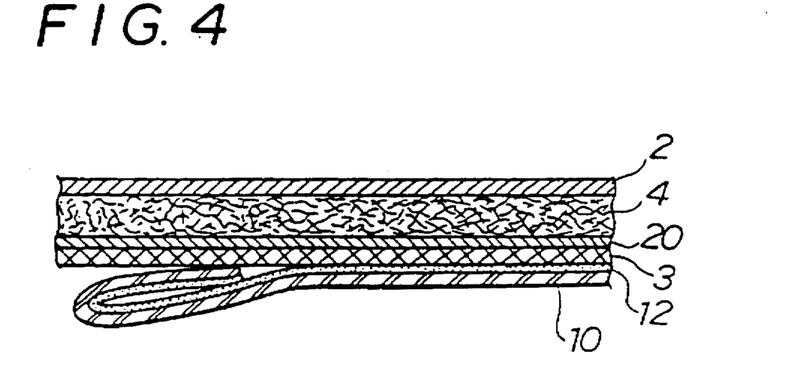
FIG. 4 is a cross-sectional view showing the cross section of the disposable diaper shown in FIG. 3 taken along the A—A line.
Figure 5:
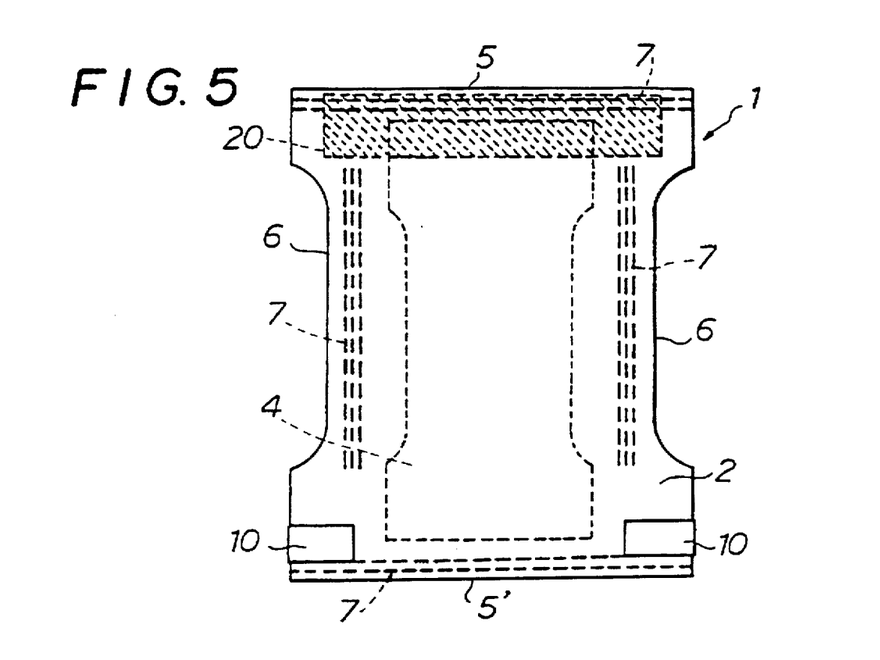
FIG. 5 is a view in which the disposable diaper shown in FIG. 3 is laid flat.
Figures 13A, 13B:
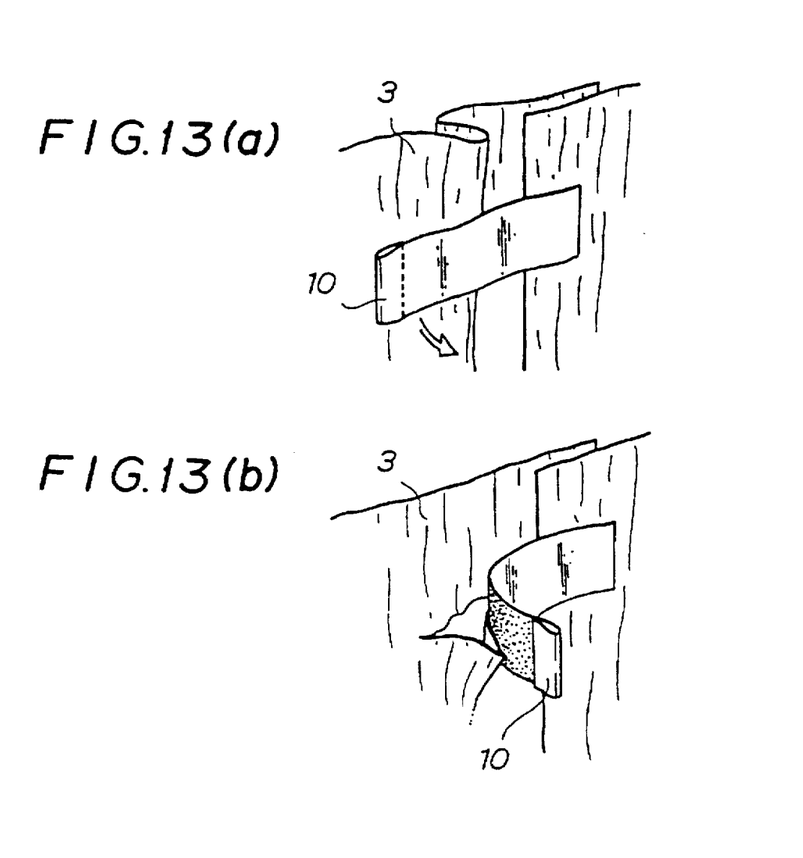
FIG. 13(a) is a schematic view showing a state in which the fastening tape is adhered improperly to the back sheet in a prior art diaper.
FIG. 13(b) is a schematic view showing a state in which the fastening tape shown in FIG. 13(a) is peeled off.

According to another embodiment of the present invention, as shown in FIGS. 3 to 5, a reinforcement film 20 is provided on an inner surface of the back sheet 3 facing the absorbent member 4. Particularly, the reinforcement film 20 is preferably provided at a body-surrounding portion of a stomach-side of the back sheet 3. The use of the reinforcement film prevents breakage of the back sheet 3 as shown in FIG. 13(b) to a greater extent even though the fastening tape 10 is fastened in such a manner as shown in FIG. 13(a).

The ratio of the area of the reinforcement film 20 to that of the back sheet is preferably smaller than ⅓, more preferably smaller than ⅕.

If the ratio exceeds ⅓, the back sheet 3 gives an unpleasant stiff feeling, the production cost is increased, and the permeability of the aforesaid permeable sheet used as the back sheet is lowered. Therefore, the ratio of ⅓ or less is preferred.

The bulk softness at the position where the reinforcement film is provided (i.e., the bulk softness of the reinforcement film and the back sheet in the transverse direction of the disposable diaper) preferably falls within the range of 50 to 300 g, more preferably within the range of 100 to 250 g. In particular, the bulk softness of the reinforcement film 20 provided at the body-surrounding portion in the stomach side of the back sheet 3 preferably falls within the range of 50 to 300 g. If the bulk softness is less than 50 g, the back sheet 3 is wrinkled when the fastening tape 10 is fastened, so that the diaper may become difficult to handle. If the bulk softness is more than 300 g, the back sheet 3 is liable to give unpleasant stiff feeling. Therefore, the above range is preferred.

The reinforcement film 20 is preferably provided on the back sheet by adhesion. The reinforcement film is preferably adhered to the back sheet by such a force that the reinforcement film does not peel from the back sheet when the fastening tape is peeled from the back sheet during or after use of the diaper. That is, the adhesive force for adhering the reinforcement film 20 to the back sheet 3 is preferably of such a degree that the reinforcement film 20 does not peel from the back sheet 3 by a force caused by the movements of the wearer during use of the diaper or by the force applied to the adhered portion where the reinforcement film 20 is adhered to the back sheet 3.

A peel strength required to peel the reinforcement film from the back sheet at 180° is preferably greater than a peel strength required to peel the fastening tape 10 from the back sheet 3 at 180°. If the peel strength required to peel the reinforcement film 20 from the back sheet 3 at 180° is smaller than the peel strength required to peel the fastening tape 10 from the back sheet at 180°, the reinforcement film 20 is peeled from the back sheet 3 when the fastening tape 10 is peeled from the back sheet 3, so that the reinforcement film 20 may unfavorably fail to exhibit its inherent performance.

A time required until the reinforcement film 20 and the back sheet 3 are peeled from each other under a load of 500 g is preferably longer than a time required until the back sheet 3 and the fastening tape 10 are peeled from each other under a load of 500 g. If the time required until the reinforcement film 20 and the back sheet 3 are peeled from each other under a load of 500 g is shorter than the time required until the back sheet 3 and said fastening tape 10 are peeled from each other under a load of 500 g, the reinforcement film 20 is caused to be peeled from the back sheet 3 during use of the diaper, so that the reinforcement film 20 may unfavorably fail to perform its inherent function.

The reinforcement film 20 preferably comprises a porous film because the porous film is more advantageous in preventing stiffness. Any porous films that is used in conventional diapers can be used with no limitation. Alternatively, the reinforcement film 20 may be of a film whose surface facing the absorbent member 4 has been exclusively subjected to release treatment.

Figure 6A:
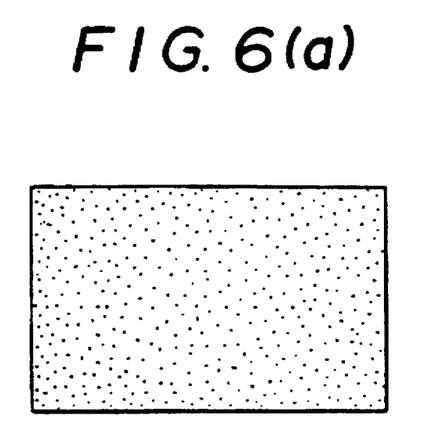
FIGS. 6(a) to 6(e) are views showing adhesion patterns of the reinforcement film to the back sheet.
Figure 6B:
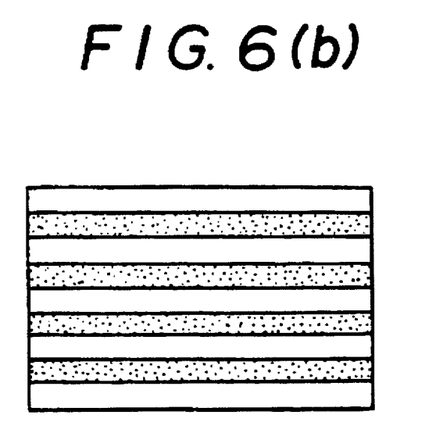
Figure 6C:
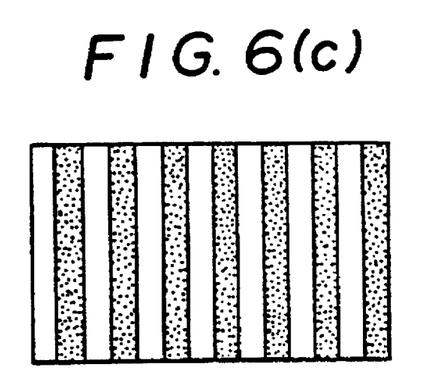
Figure 6D:
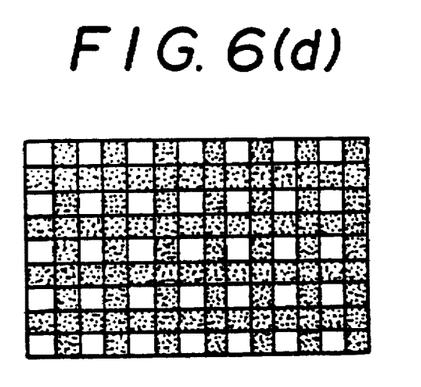
Figure 6E:
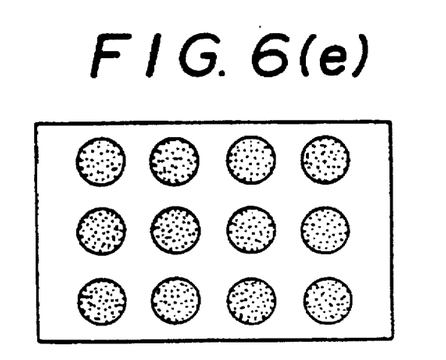

The adhesion of the reinforcement film to the back sheet 3 can be effected with no limitation by conventional adhesives. The adhesion is preferably effected in accordance with the adhesion patterns shown in FIGS. 6(a) to 6(e), wherein FIG. 6(a) illustrates that adhesion is effected on the entire surface; FIG. 6(b) illustrates that adhesion is effected in accordance with a laterally-striped pattern; FIG. 6(c) illustrates adhesion is effected in accordance with a vertically-striped pattern; FIG. 6(d) illustrates that adhesion is effected by applying adhesive agents in a grid pattern; FIG. 6(e) illustrates that adhesion is effected by applying adhesive agent in a circular pattern. In particular, the pattern shown in FIG. 6(a) in which adhesion is effected on the entire surface and the pattern shown in FIG. 6(d) in which adhesion is effected by applying adhesive agents in a grid pattern are preferred because the load is dispersed all over the back sheet when the fastening tape is peeled.

Figure 7:
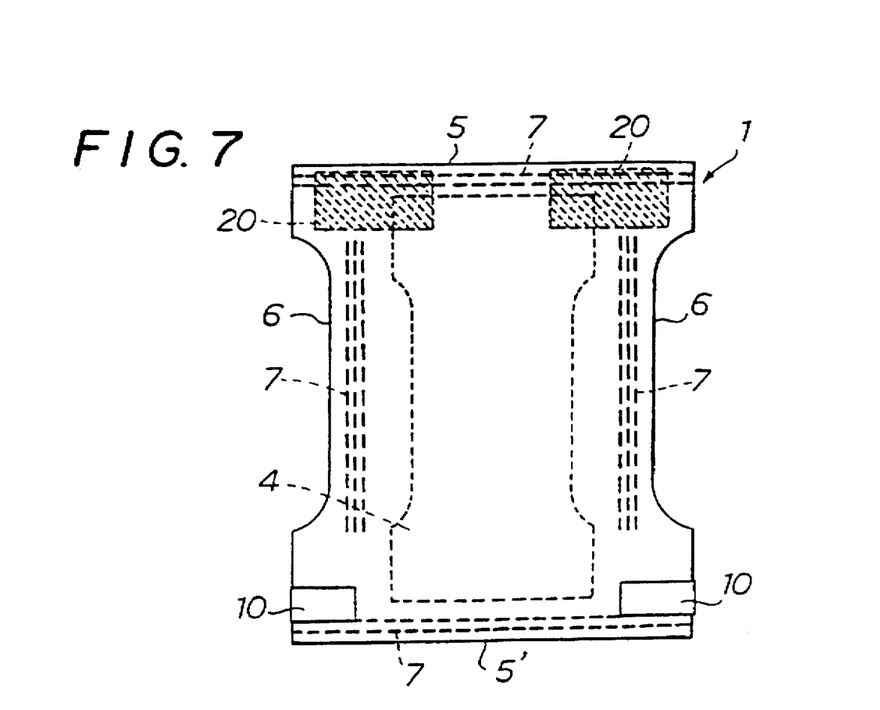
FIG. 7 is a view in which a diaper according to still another embodiment of the present invention is laid flat (FIG. 7 corresponds to FIG. 5)

Alternatively, the reinforcement film 20 may be provided as shown in FIG. 7 (which corresponds to FIG. 5) in which a disposable diaper according to still another embodiment of the present invention is laid flat. The same features as those in the embodiment illustrated in FIG. 5 will not be describe in detail hereinbelow, and the descriptions in terms of the above embodiment are also applied to the embodiment illustrated in FIG. 7.

In the disposable diaper shown in FIG. 7, the reinforcement films 20 are provided on both the right and left sides (portions other than the central portion) of the body-surrounding portion in the stomach side of the diaper.

As is apparent for those skilled in the art from the foregoing descriptions, the manner of providing the reinforcement film 20 is not particularly limited so far as the reinforcement film is provided at the portion where the fastening tape 10 is fastened during use.

The physical properties are measured in the manner described below.

Figures 8A, 8B:
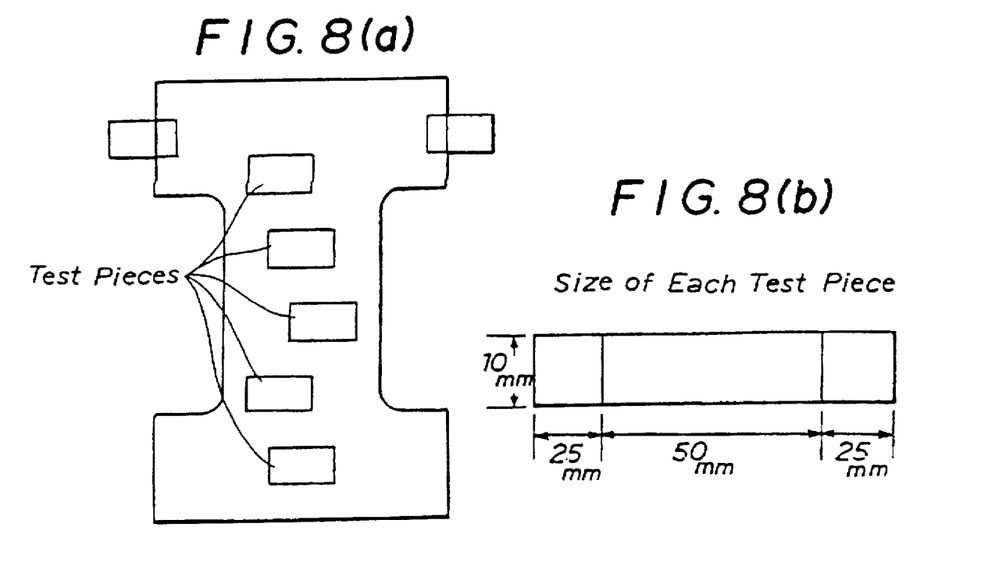
FIGS. 8(a) and 8(b) are schematic views showing the sampling regions and the size of the test piece in the measurement of the tensile load at 3% elongation, respectively.

1. Tensile load of back sheet at 3% elongation
(1) Measuring apparatus
Tensilon universal testing apparatus, tensile test mode (supplied by Orientec Co., Ltd.)
(2) Test Pieces
As illustrated in FIG. 8(a), test pieces are taken from five positions of the diaper. (At this time, in cases where adhesive agents or absorbent papers cling to the back sheet, they should be removed by an organic solvent such as toluene to such an extent that the back sheet may not be affected adversely.) As illustrated in FIG. 8(b), the size of each test piece is 10 mm×(25 mm+50 mm+25 mm).
(3) Measurement conditions
   i) Measuring environment: Temperature 20° C. Humidity 65% RH
   ii) Tensile conditions: Distance between chucks; 50 mm Rate of elongation; 300 mm/min
(4) Measurement results
The tensile strength of each test piece at 3% elongation (when the distance between chucks of 50 mm is increased to 51.5 mm) is measured. The mean value of the values measured for five test pieces is calculated.

Figure 9A:
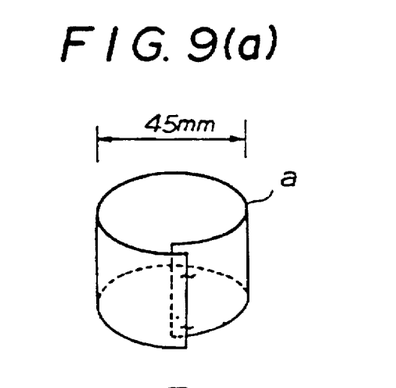
FIGS. 9(a), 9(b) and 9(c) are schematic views showing how a specimen is formed for the measurement of the bulk softness.
Figure 9B:
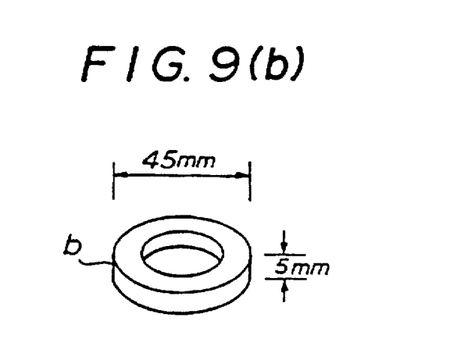
Figure 9C:
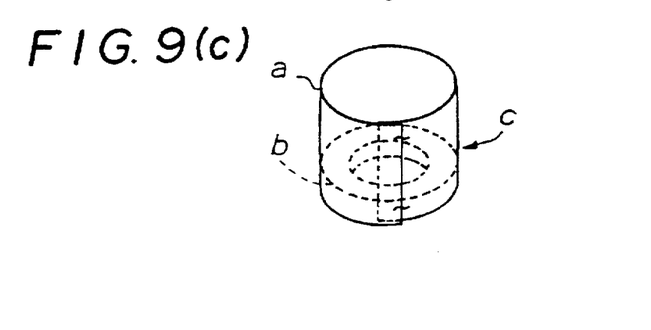

2. Bulk softness of back sheet
(1) Measuring apparatus
Tensilon universal testing apparatus, compression test mode (supplied by Orientec Co., Ltd.)
(2) Test Pieces
   i) Test pieces are taken from the same positions as in the sampling for the measurement of the tensile load of the back sheet at 3% elongation in item 1. However, the size of the test pieces is 30 mm ×150 mm (The test pieces were taken in the transverse direction of the diaper.).
   ii) Specimen: As illustrated in FIG. 9(a), each test piece is formed into a cylinder a having a diameter of 45 mm in such a manner that the outer side of the cylinder corresponds to the outer surface of the back sheet. The upper and lower ends of the overlapped portion are fixed by using a stapler. Thereafter, a ring b made of polyvinyl chloride shown in FIG. 9(b) is fitted to the lower portion of the cylinder a. In this manner, a specimen c shown in FIG. 9(c) is obtained.
(3) Measurement conditions
   i) Measuring environment: Temperature 20° C. Humidity 65% RH
   ii) Compressing conditions: Rate of compression; 10 mm/min
(4) Measurement results
The maximum strength of each test piece is measured when the test piece is compressed by 20 mm. The mean value of the values measured for five test pieces is calculated and taken as the bulk softness.

3. Break strength of back sheet
The test is carried out in the same manner as that in the measurement of the tensile load of the back sheet at 3% elongation in item 1. The load at the time of breakage is measured and taken as the break strength (The break strength is measured in the transverse direction of the diaper).

Figure 10:
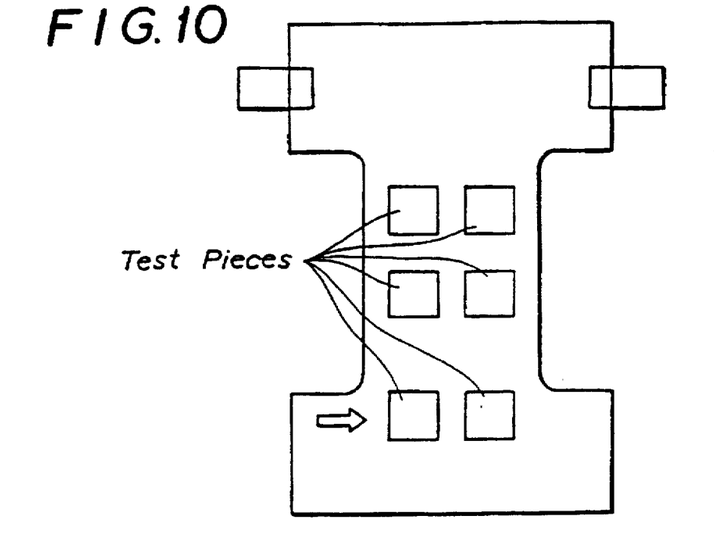
FIG. 10 is a schematic view showing the sampling regions when the retention time is measured.
Figure 11:
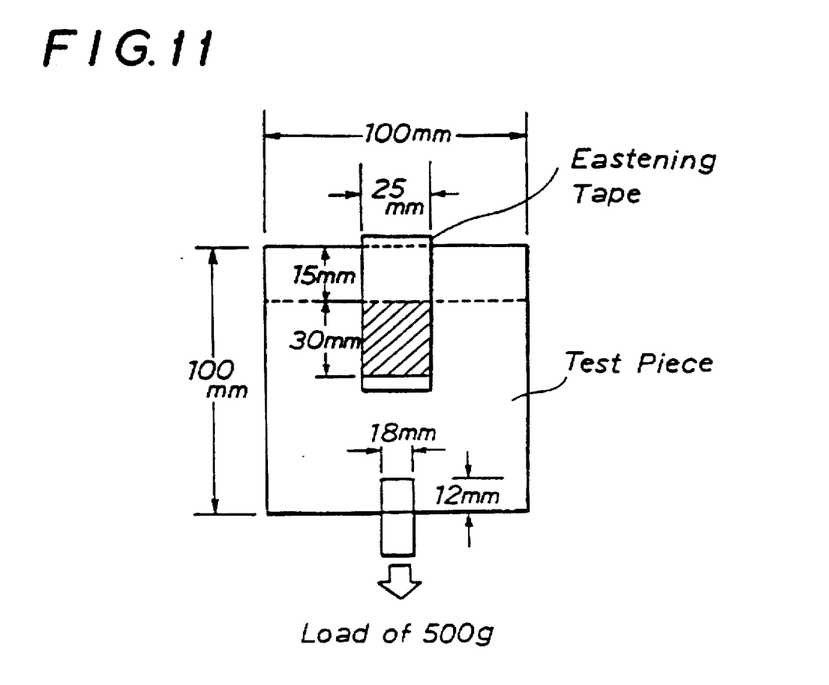
FIG. 11 is a schematic view showing how the retention time is measured.

4. Retention time of fastening tape
(1) Measuring apparatus
Retention force tester with constant temperature bath (supplied by Tester Sangyo Co., Ltd.)
(2) Test Pieces
As illustrated in FIG. 10, test pieces are taken from six positions of the diaper. (At this time, in cases where adhesive agents or absorbent papers cling to the back sheet, they should be removed by an organic solvent such as toluene to such an extend that the back sheet may not be affected adversely.) The size of each test piece is 100 mm×100 mm.
(3) Measurement conditions
   i) Measuring environment: Temperature 40° C.
   ii) Load conditions: 500 g
(4) Measurement results
As illustrated in FIG. 11, a fastening tape is adhered to the test piece in such a manner that the area of adhesion indicated by hatching in FIG. 11 may be 25 mm×30 mm. A load of 500 g is applied vertically (i.e., in the direction indicated by the arrow in FIG. 11). The retention time is then measured. The measurements are carried out for each of the six test pieces, and the mean value of the measured values is calculated. At this time, the fastening tape is adhered to each test piece in such a manner that the longitudinal direction of the fastening tape may coincide with the transverse direction (the direction to which the longitudinal direction of the diaper is perpendicular) of the diaper in each test piece, which transverse direction is indicated by the arrow in FIG. 11. Adhesion of the fastening tape to the test piece is carried out by a single reciprocating motion of a 200 g rubber roller on the fastening tape.

5. Peel strength at 180°

Figures 12A, 12B:
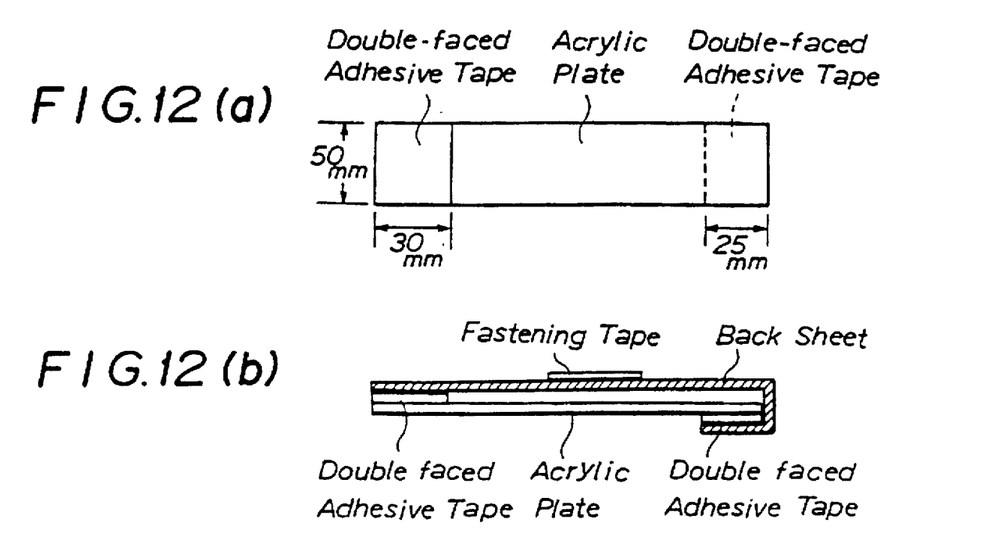
FIG. 12(a) is a plan view showing an adherend which is used for the measurement of the peel strength at 180°.
FIG. 12(b) is a side view showing how a fastening tape is adhered to the adherend.

An adherend shown in FIG. 12(a) is obtained by adhering double-faced adhesive tapes (MD 30 mm) to an acrylic plate (50 mm×125 mm×3 mm) and then adhering the back sheet to the double-faced adhesive tapes in such a manner that the back sheet is not damaged. Thereafter, as illustrated in FIG. 12(b), a fastening tape is adhered to the adherend over an area of 25 mm×20 mm. The fastening tape is adhered under pressure by a single reciprocating motion of a 25 mm-wide, 200 g rubber roller on the fastening tape. The specimen thus obtained is allowed to stand for 24 hours at 40° C. and 80% RH. The specimen is then allowed to stand at room temperature for 30 minutes. Measurement in the peel strength at 180° is then carried out under the conditions described below, and the mean load is calculated and taken as the adhesive force (g/25 mm) of the fastening tape with respect to the back sheet. The measurements are carried out for five specimens, and the mean value of the measured values is calculated. After the measurements, the measured values are converted into values per 10 mm tape width [measured value×(10/25)].

(1) Measuring apparatus Tensilon universal tensile testing apparatus (2) Test pieces Sampling positions and the size of the test pieces (150×50 mm) are the same as those in the measurement of the tensile load of the back sheet at 3% elongation in item 1.

(3) Measurement conditions The measurement conditions are the same as those in the measurement of the tensile load of the back sheet at 3% elongation in item 1.

(4) Measurement results

The mean value of the measured peel strength values for the five specimens is calculated.

Hereinafter, the present invention will be described in more detail by way of examples, but it should be understood that the present invention is not construed as being limited thereto.

EXAMPLE

A film A and a film B were prepared in the manner described below. Also, a tape T was prepared in the manner described below. Disposable diapers as shown in FIGS. 1 and 2 were prepared by using each of the film A and the film B as the back sheet and using the tape T as the fastening tape.

As for the disposable diapers thus obtained, the tensile load of the back sheet at 3% elongation, the bulk softness of the back sheet, the break strength of the back sheet, the peel strength at 180° and the retention time of the fastening tape were measured in accordance with the measurement methods described above. Also, after the use of each disposable diaper, tests were carried out as to breakage of the back sheet, detachment of the fastening tape, and the skin feel of the back sheet. The measurement and test results shown in Table 1 were obtained. (Preparation of Film A)

A composition containing 70 parts by weight of a polypropylene (supplied under the trade name "XF1932" by Chisso Petrochemical Co., Ltd.) and 30 parts by weight of liquid paraffin (supplied under the trade-name "PW90" by Idemitsu Petrochemical Co., Ltd.) was introduced into a twin-screw extruder, and pellets were thereby prepared. A film was then formed from the pellets by using an air-cooled inflation molding machine. The film was then oriented monoaxially in a draw ratio of 1.5, and the film A was thereby obtained. The thickness of the film A thus obtained was approximately 35μm. The film A was a porous film having a moisture permeability of 1.9 g/100 cm $^2$.hr. (Preparation of Film B)

A film B having a thickness of approximately 35 μm was obtained in the same manner as that for the film A, except that, in lieu of the aforesaid composition, a composition containing 66 parts by weight of a polypropylene (supplied under the trade name "B200" by Mitsui Petrochemical Industries, Ltd.), 4 parts by weight of a nucleating agent master batch (supplied under the trade name "EC-1" by EC Chemical Co., Ltd., concentration 2 wt.%), and 30 parts by weight of liquid paraffin (supplied under the trade name "PW90" by Idemitsu Petrochemical Co., Ltd.) was used. The film B was a porous film having a moisture permeability of 2.0 g/100 cm 2.hr. (Tape T)

An adhesive agent (supplied under the trade name "Panel Master AM936" by Kanebo NSC K.K., and containing, as a predominant component, an acrylic resin) was applied to a PET film having a thickness of 50 μm and serving as a support of the fastening tape. The thickness of the adhesive surface was 30 μm. In this manner, the tape T was obtained.

Comparative Example

The measurements and tests were carried out in the same manner as in the Example for the commercially available L-sized diapers having a target tape (Samples P and K) and the commercially available L-sized diaper having no target tape (Sample J), which are shown in Table 1. The results shown in Table 1 were obtained.

TABLE 1

| | | Back Sheet | | | Peal Strength at 180° (g/cm) | Retention Time (minutes) | State of the diapers after use | | Skin Feel of the Back Sheet* |
| | | Break Strength (g/cm) | Bulk Softness (g) | Tensile Load (g/cm) | | | Breakage of BS | Failure in Adhesion of FT | |
| --- | --- | --- | --- | --- | --- | --- | --- | --- | --- |
| Example | Film A Tape T | 650 | 35 | 170 | 300 | ≧60 | Not Observed | 0/100 | S |
| | Film B Tape T | 450 | 30 | 150 | 400 | ≧30 | Not Observed | 0/100 | S |
| Compara. Example | Commercially Available Diaper P | 320 | 28 | 95 | 280 | ≧60 | On TT (Not Observed) On BS (Broken) | 0/100 | S |

TABLE 1-continued

| | Back Sheet | | Peal | | | State of the diapers after use | | Skin Feel |
|---|---|---|---|---|---|---|---|---|
| | Break Strength (g/cm) | Bulk Softness (g) | Tensile Load (g/cm) | Strength at 180° (g/cm) | Retention Time (minutes) | Breakage of BS | Failure in Adhesion of FT | of the Back Sheet* |
| Commercially Available Diaper K (with TT) | 200 | 17 | 80 | 200 | ≧60 | On TT (Not Observed) On BS (Broken) | 0/100 | S |
| Commercially Available Diaper J (no TT) | 600 | 46 | 200 | 230 | 6 | Not Observed | 5/100 | F |

*The questionnairing was conducted on 20 mothers. "F" indicates that more than a half of the mothers judge that the back sheet gives a stiff feeling while "S" indicates that less than a half of the mothers judge that the back sheet gives a stiff feeling. "BS" indicates the back sheet. "TT" indicates the target tape, and "FT" indicates the fastening tape.

INDUSTRIAL APPLICABILITY

In the disposable diaper in accordance with the present invention, breakage of the back sheet or detachment of the fastening tape can be prevented without providing the target tape. Further, the diaper is excellent in softness of the back sheet and feeling during use.

Further, even though the fastening tape is fastened improperly as shown in FIG. 13 (a), the back sheet does not break since the reinforcement film is provided on the inner surface of the back sheet facing the absorbent member.

Particularly, in the conventional disposable diaper, even though a moisture permeable sheet is employed as the back sheet, the moisture permeable back sheet fails to exhibit permeability at the portion covered with the target tape because the target tape prevents moisture from permeating. In contrast, the disposable diaper in accordance with the present invention, wherein no target tape is provided and the porous sheet having moisture permeability is employed as the back sheet, exhibits excellence in preventing stuffiness during use of the diaper.

Further, where the porous sheet is prepared from the above polymer composition, the porous sheet thus prepared exhibits an excellent performance as a back sheet of a diaper.

Many other variations and modifications of the invention will be apparent to those skilled in the art without departing from the spirit and scope of the invention. The above-described embodiments are, therefore, intended to be merely exemplary, and all such variations and modifications are intended to be included within the scope of the invention as defined in the appended claims.

We claim:

1. A disposable diaper comprising:

a liquid permeable topsheet;

a liquid impermeable back sheet;

an absorbent member interposed between and attached to said topsheet and said back sheet;

a fastening tape for securing said diaper when said diaper is worn by a wearer, said fastening tape being provided with a folding section at which said fastening tape is to be folded back; and a release tape to which, when said fastening tape is not in service and is folded back, an adhesive surface of said fastening tape is to be adhered, said fastening tape is adhered to said back sheet when said fastening tape is in service, said disposable diaper having physical strength properties wherein:

a tensile load of said back sheet at 3% elongation in a transverse direction of said disposable diaper falls within the range of 100 g/cm to 300 g/cm, and a bulk softness of said back sheet is 55 g or less, said transverse direction being parallel to a waist portion of the diaper;

a peel strength required to peel said fastening tape from said back sheet at 180° is 400 g/cm or less, said peel strength being measured after said fastening tape adhered to said back sheet has been allowed to stand for 24 hours at 40° C. and 80% RH, and a time required until said fastening tape and said back sheet are peeled from each other under a load of 500 g is 10 minutes or longer; and an outer surface of said back sheet is not provided with a target tape to which, when said fastening tape is in service, the adhesive surface of said fastening tape is to be adhered.

2. The disposable diaper as defined in claim 1, wherein a break strength of said back sheet is 250 g/cm or more.

3. The disposable diaper as defined in claim 1, wherein said tensile load falls within the range of 100 g/cm to 200 g/cm, and said bulk softness is 45 g or less.

4. The disposable diaper as defined in claim 1, wherein said back sheet is a porous sheet and has a moisture permeability falling within the range of 0.5 to 4.0 g/100 cm 2.hr.

5. The disposable diaper as defined in claim 4, wherein said porous sheet is made of a molded melt blended solution comprising crystalline polyolefin and a compound with which said crystalline polyolefin will dissolve at or above the melting point of said crystalline polyolefin but which will phase separate below the melting point of said microporous due to stretching in crystalline polyolefin, and least in one direction.

6. The disposable diaper as defined in claim 1, further comprising a reinforcement film provided on an inner surface of said back sheet facing said absorbent member.

7. The disposable diaper as defined in claim 6, wherein said reinforcement film is provided at a body-surrounding portion in a stomach side of said back sheet, and a bulk softness at the position where the reinforcement film is provided falls within the range of 50 to 300 g.

8. The disposable diaper as defined in claim 6, wherein said reinforcement film is adhered to said back sheet by such a force that said reinforcement film does not peel from said back sheet when said fastening tape is peeled from said back sheet during or after use of the diaper.

9. The disposable diaper as defined in claim 6, wherein a peel strength required to peel said reinforcement film from said back sheet at 180° is greater than said peel strength required to peel said fastening tape from said back sheet at 180°.

10. The disposable diaper as defined in claim 6, wherein a time required until said reinforcement film and said back sheet are peeled from each other under a load of 500 g is longer than said time required until said back sheet and said fastening tape are peeled from each other under a load of 500 g.

11. The disposable diaper as defined in claim 6, wherein said reinforcement film comprises a porous film.

* * * * *